(12) United States Patent
Bovin et al.

(10) Patent No.: US 9,915,653 B2
(45) Date of Patent: Mar. 13, 2018

(54) FACILE LABORATORY METHOD FOR LOCALISING BIOMOLECULES TO THE SURFACE OF CELLS AND VIRUSES

(76) Inventors: Nikolai Vladimirovich Bovin, Moscow (RU); Stephen Michael Henry, Auckland (NZ); Igor Leonidovich Rodionov, Moscow Region (RU)

(*) Notice: Subject to any disclaimer, the term of this patent is extended or adjusted under 35 U.S.C. 154(b) by 170 days.

(21) Appl. No.: 14/241,578

(22) PCT Filed: Aug. 31, 2012

(86) PCT No.: PCT/NZ2012/000156
§ 371 (c)(1),
(2), (4) Date: Nov. 11, 2014

(87) PCT Pub. No.: WO2013/081471
PCT Pub. Date: Jun. 6, 2013

(65) Prior Publication Data
US 2015/0064690 A1    Mar. 5, 2015

(30) Foreign Application Priority Data

Aug. 31, 2011 (NZ) ........................ 594941
May 4, 2012 (NZ) ........................ 599802

(51) Int. Cl.
| | | |
|---|---|---|
| *G01N 33/555* | (2006.01) | |
| *G01N 33/554* | (2006.01) | |
| *G01N 33/68* | (2006.01) | |
| *G01N 33/92* | (2006.01) | |
| *G01N 33/571* | (2006.01) | |

(52) U.S. Cl.
CPC ......... *G01N 33/555* (2013.01); *G01N 33/554* (2013.01); *G01N 33/571* (2013.01); *G01N 33/6815* (2013.01); *G01N 33/92* (2013.01); *G01N 2333/005* (2013.01); *G01N 2333/20* (2013.01)

(58) Field of Classification Search
None
See application file for complete search history.

(56) References Cited

U.S. PATENT DOCUMENTS

| 7,598,421 B2 | 10/2009 | Hailes et al. |
|---|---|---|
| 2011/0003969 A1* | 1/2011 | Kellogg ........... A61K 47/48215 530/303 |

FOREIGN PATENT DOCUMENTS

| WO | WO 2009/048343 A1 | 4/2009 |
|---|---|---|
| WO | WO 2010/143983 | * 12/2010 |
| WO | WO 2012/040825 A1 | 4/2012 |
| WO | WO 2013/081471 A2 | 6/2013 |

OTHER PUBLICATIONS

Blake et al ('FSL Constructs: a simple method for modifying cell/virion surfaces with a range of biological markers without affecting their viability' Journal of Visualized Experiments (54) published Aug. 5, 2011 pp. 1-9).*
Hossen et al ('Ligand-based targeted delivery of a peptide modified nanocarrier to endothelial cells in adipose tissue' Journal of Controlled Release v147 2010 pp. 261-268).*
Henry, S., et al; Technical Bulletin: FSL-RFG(Maleimide) FSL Construction Kit, Version 20110928, Kodebiotech.com, Sep. 28, 2011 [retrieved on Feb. 23, 2014]. Retrieved from the Internet: <URL: http://aut.researchgateway.ac.nz/bistream/handle/10292/2241/20110928%20FSL%20RFG(Mal).pdf?sequence-2>; 10 pgs.
PCT International Search Report, Int'l Application No. PCT/NZ12/00156, Int'l filed Aug. 31, 2012 (3 pgs).

* cited by examiner

*Primary Examiner* — Karlheinz R. Skowronek
*Assistant Examiner* — Ronald T Niebauer
(74) *Attorney, Agent, or Firm* — Nixon & Vanderhye P.C.

(57) ABSTRACT

Method of localizing a sulfhydryl (—SH) group containing biomolecule to the surface of a cell membrane by mixing in a volatile reaction buffer a molar excess of the sulfhydryl (—SH) group containing biomolecule with a lipid conjugated maleimide of the structure F-S-L as defined in the specification to provide a reaction mix, incubating the reaction mix for a time and at a temperature sufficient to allow all the lipid conjugated maleimide to have reacted with the sulfhydryl (—SH) group, and freeze-drying the reaction mix to remove the volatile reaction buffer and provide a reaction product. An aqueous solution of the reaction product is contacted with the cell membrane.

19 Claims, 4 Drawing Sheets

FACILE LABORATORY METHOD FOR LOCALISING BIOMOLECULES TO THE SURFACE OF CELLS AND VIRUSES

This application is the U.S. national phase of International Application No. PCT/NZ2012/000156 filed Aug. 31, 2012 which designated the U.S. and claims priority to New Zealand Patent Application Nos. 594941 filed Aug. 31, 2011, and 599802 filed May 4, 2012, the entire contents of each of which are hereby incorporated by reference.

FIELD OF INVENTION

The invention relates to a facile method of localising sulfhydryl (—SH) group containing biomolecules, in particular peptides, to the membranes of living cells and enveloped viruses and a kit for use in a biological laboratory in accordance with the method.

BACKGROUND ART

Historically, the capabilities of biological and chemical laboratories have resulted in biological and chemical research being performed at separate locations. Bioconjugation is the process of coupling two biomolecules together in a covalent linkage (Hermanson (2008)). Bioconjugation is employed to study the function of biomolecules in living systems. The methods employed require the capabilities of both biological and chemical laboratories.

Water dispersible constructs of the general structure F-S-L (where F is a functional moiety, S is a spacer and L is a lipid) that spontaneously incorporate into lipid bilayers (KODE™ Constructs) have provided researchers with a means of functionalising the surface of living cells and membrane bound organelles and virions without the need for the capabilities of a chemical laboratory (Bovin et al (2005), Carter et al (2007), Korchagina et al (2008) and Bovin et al (2009)).

Notwithstanding these advances, the use of KODE™ Constructs by researchers in biological laboratories is for the most part restricted to the use of KODE™ Constructs that are available commercially. A method of preparing bespoke KODE™ Constructs capable of being employed in a biological laboratory using the equipment routinely available in those facilities is desirable.

Is an object of the invention described in this specification to provide such a method. Is an object of the invention described in this specification to provide a kit to facilitate the use of such method. These objects are to be read disjunctively with the object to at least provide a useful choice.

STATEMENT OF INVENTION

In a first aspect the invention provides a method of localising a sulfhydryl (—SH) group containing biomolecule to a surface comprising the steps:
1. Mixing in a volatile reaction buffer a molar excess of the sulfhydryl (—SH) group containing biomolecule with a lipid conjugated maleimide of the structure F-S-L to provide a reaction mix;
2. Incubating the reaction mix for a time and at a temperature sufficient to allow substantially all the lipid conjugated maleimide to have reacted;
3. Drying the reaction mix to remove the reaction buffer and provide a reaction product; and
4. Contacting a solution of the reaction product with the surface, where:
F is

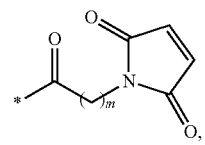

S is selected from the group consisting of:

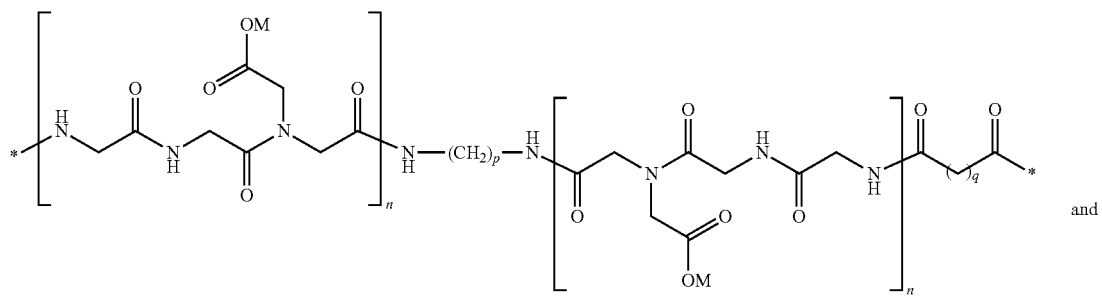

and

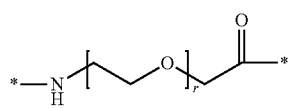

L is an amide linked diacyl- or dialkyl-glycerophospholipid,
m is the integer 1, 2 or 3,
M is a monovalent cation or substituent,
n is the integer 1, 2 or 3,
p is the integer 1, 2 or 3,
q is the integer 3, 4 or 5, and
the median value of r is 6, 7, 8, 9, 10, 11, 12, 13, 14, 15 or 16.

Preferably, the sulfhydryl (—SH) group is a cysteine residue (Cys).

Preferably, the sulfhydryl (—SH) group containing biomolecule is a peptide. More preferably, the sulfhydryl (—SH) group containing biomolecule is a peptide with a cysteine residue (Cys) at or proximal to the C-terminus of the peptide. Most preferably, the sulfhydryl (—SH) group containing biomolecule is a peptide with a cysteine residue (Cys) at the C-terminus.

thanolamine or a phosphatidylserine. Yet more preferably, L is an amide linked phosphatidylethanolamine. Most preferably, L is 1,2-O-dioleoyl-sn-glycero-3-phosphatidylethanolamine (DOPE).

Preferably,

S is

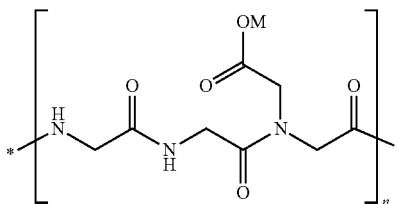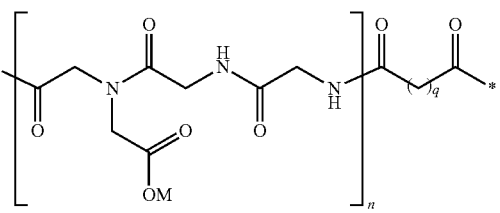

Preferably, the surface is a membrane. More preferably, the surface is a cell membrane or the membrane of an enveloped virus. Yet more preferably, the surface is a cell membrane. Most preferably, the surface is the cell membrane of a red blood cell.

The method permits the localising of sulfhydryl (—SH) group containing biomolecules to the membranes of living cells.

Preferably, the incubating is for a time greater than 8 hours and at room temperature (circa 25° C.).

Preferably, the drying is by freeze-drying.

Preferably, the solution of the reaction product is an aqueous solution of the reaction product. More preferably, the solution of the reaction product is an aqueous saline solution of the reaction product.

The method excludes a step of purifying the reaction product by conventional separation methods such as column chromatography prior to preparing the solution of the reaction product and the step of contacting the solution of the reaction product with the surface.

Preferably, M is H or $CH_3$. More preferably, M is H.

In a second aspect the invention provides a kit packaged with directions for use in a method of localising a sulfhydryl (—SH) group containing biomolecule to a surface comprising:

1. an amount of a lipid conjugated maleimide of the structure F-S-L; and
2. a volume of a volatile reaction buffer, where:

F is

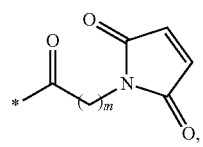

[followed by page 5]

S is selected from the group consisting of:

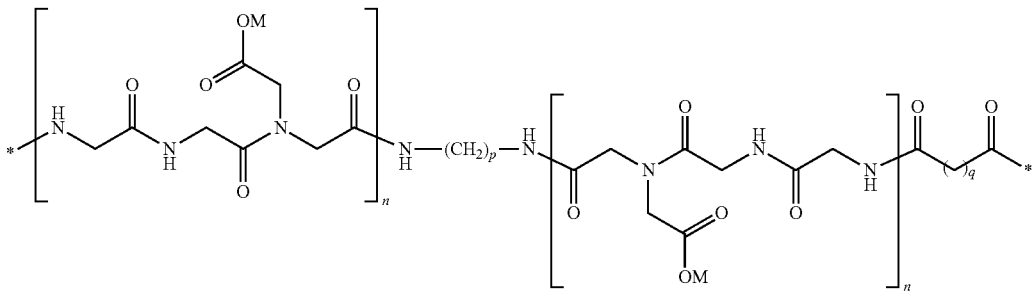

Preferably, the volatile reaction buffer is 0.1M 4-methylmorpholine formate (4-MMF) in 30% isopropanol (IPA) at a pH in the range 6.5 to 6.7.

Preferably, m is the integer 2. Preferably, n is the integer 2.

Preferably, p is the integer 2. Preferably, q is the integer 4. More preferably, each of m, n and p are the integer 2 and q is the integer 4. Preferably, the median value of r is 6.

Preferably, L is an amide linked diacylglycerophospholipid. More preferably, L is an amide linked phosphatidyleand

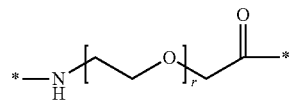

L is an amide linked diacyl- or dialkyl-glycerophospholipid, m is the integer 1, 2 or 3,
M is a monovalent cation or substituent,
n is the integer 1, 2 or 3,
p is the integer 1, 2 or 3,
q is the integer 3, 4 or 5, and
the median value of r is 6, 7, 8, 9, 10, 11, 12, 13, 14, 15 or 16.

Preferably, the sulfhydryl (—SH) group is a cysteine residue (Cys).

Preferably, the sulfhydryl (—SH) group containing biomolecule is a peptide. More preferably, the sulfhydryl (—SH) group containing biomolecule is a peptide with a cysteine residue (Cys) at or proximal to the C-terminus of the peptide. Most preferably, the sulfhydryl (—SH) group containing biomolecule is a peptide with a cysteine residue (Cys) at the C-terminus.

Preferably, the volatile reaction buffer is 0.1M 4-methylmorpholine formate (4-MMF) in 30% isopropanol (IPA) at a pH in the range 6.5 to 6.7.

Preferably, m is the integer 2. Preferably, n is the integer 2.

Preferably, p is the integer 2. Preferably, q is the integer 4. More preferably, each of m, n and p are the integer 0.2 and q is the integer 4. Preferably, the median value of r is 6.

Preferably, L is an amide linked diacylglycerophospholipid. More preferably, L is an amide linked phosphatidylethanolamine or a phosphatidylserine. Yet more preferably, L is an amide linked phosphatidylethanolamine. Most preferably, L is 1,2-O-dioleoyl-sn-glycero-3-phosphatidylethanolamine (DOPE).

Preferably,
S is

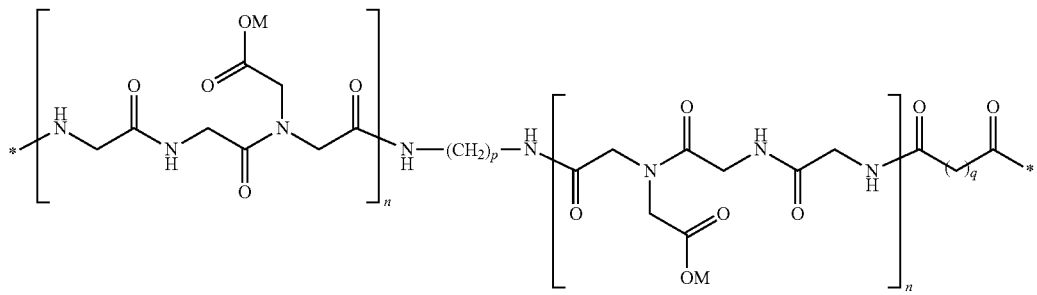

Preferably, M is H or $CH_3$. More preferably, M is H.

In the description and claims of this specification the following acronyms, terms and phrases have the meaning provided:

"Comprising" means "including", "containing" or "characterized by" and does not exclude any additional element, ingredient or step.

"Consisting of" means excluding any element, ingredient or step not specified except for impurities and other incidentals.

"Localised" means associated with a surface by non-covalent interactions between the molecule comprising the localised entity and the surface (and "localising" and "localisation" have a corresponding meaning).

"Kodecyte" means a cell modified by incorporation into the cell membrane of a construct of the general structure F-S-L (where F is a functional moiety, S is a spacer selected to provide a water dispersible construct and L is a lipid).

"Kodevirion" means an enveloped virus particle modified by incorporation into the enveloping membrane of a construct of the general structure F-S-L (where F is a functional moiety, S is a spacer selected to provide a water dispersible construct and L is a lipid).

"PBS" denotes phosphate buffered saline.

"Proximal" means in the vicinity of the specified location. For the avoidance of doubt the phrase "proximal to the C-terminus of the peptide" means within x amino acid residues of the C-terminus (where the peptide consists of 'x' amino acid residues).

"Reaction product" means the product of a reaction prior to purification.

"Saline" means a solution of one or more salts.

"Synthetic" means prepared by chemical synthesis.

"Water soluble" means, in the context of describing the properties of constructs of the general structure F-S-L (where F is a functional moiety, S is a spacer and L is a lipid), a stable, single phase system is formed when the construct is contacted with water or saline (such as PBS) at a concentration of at least 100 μg/mL at a temperature of 25° C. in the absence of organic solvents or detergents. The terms "soluble" and "dispersible" are used synonymously.

It will be recognised that the phosphate moiety of a phospholipid is often protonated, but the proton ($H^+$) may be replaced by another monovalent cation such as $Na^+$, $K^+$, $NH_4^+$ or triethylamine ($[NH(CH_2CH_3)_3]^+$). Similarly, the primary and secondary amino functions of a construct may also be protonated. The constructs prepared according to the method described in this specification may therefore be prepared as a range of salts, including pharmaceutically acceptable salts.

The carboxylate residues of the moiety designated 'CMG' (Bovin et al (2009)) may be protonated, associated with another monovalent cation such as $Na^+$, $K^+$, $NH_4^+$ or triethylamine ($[NH(CH_2CH_3)_3]^+$) or covalently bound by amidation or esterification to a monovalent substituent to provide a substituted derivative such as the moiety designated 'MCMG'.

where the suffix "-al" is employed in respect of the substituents $R_1$ and $R_2$ of a diacyl lipid, an aldehyde structure is intended as exemplified by cis-9-octadecenal of the structure:

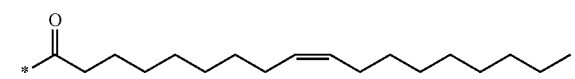 [SMILES: *C(=O)CCCCCCC/C=C\CCCCCCCC]

Where the suffix "-yl" is employed in respect of the substituents $R_1$ and $R_2$ of a dialkyl lipid, an alkyl structure is intended as exemplified by cis-9-octadecenyl of the structure:

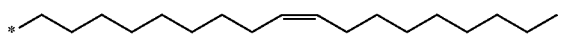

In the absence of the stereochemistry at a chiral centre being shown, the representations of the structures of compounds comprising one or more chiral centres encompass the distereoisomers, enantiomers and mixtures thereof of the compounds, with the proviso that where the representation is of the structure of a compound or a portion of the structure of a compound of biological origin, the structure or portion of the structure represented is limited to structures or portions of structures that are functionally equivalent to the structure or portion of the structure of the compound of biological origin.

An asterisk (*) is used to represent a point of covalent attachment to another moiety and does not indicate an atom. Specifically, in the representations of the moieties F, S and L of the lipid conjugated maleimide of the structure F-S-L the asterisk denotes the point of covalent attachment to the immediately adjacent moiety.

The amino acid residues of peptides are identified according to Table 3 of Appendix 2 of Annex C of the Administrative Instructions under the Patent Cooperation Treaty dated 7 Feb. 2007 and in accordance with the convention:

["amino (N) terminus"]H$_2$N-XaaXaaXaa . . . XaaXaaXaa-COOH ["carboxy (C) terminus"]

The terms "first", "second", "third", etc. used with reference to elements, features or integers of the subject matter defined in the Statement of Invention and Claims, or when used with reference to alternative embodiments of the invention are not intended to imply an order of preference.

Where concentrations or ratios of reagents are specified the concentration or ratio specified is the initial concentration or ratio of the reagents. Where values are expressed to one or more decimal places standard rounding applies. For example, 1.7 encompasses the range 1.650 recurring to 1.7499 recurring.

The invention will now be described with reference to a General Example, a Specific Example, and the figures of the accompanying drawings pages.

DETAILED DESCRIPTION

Figure 1:
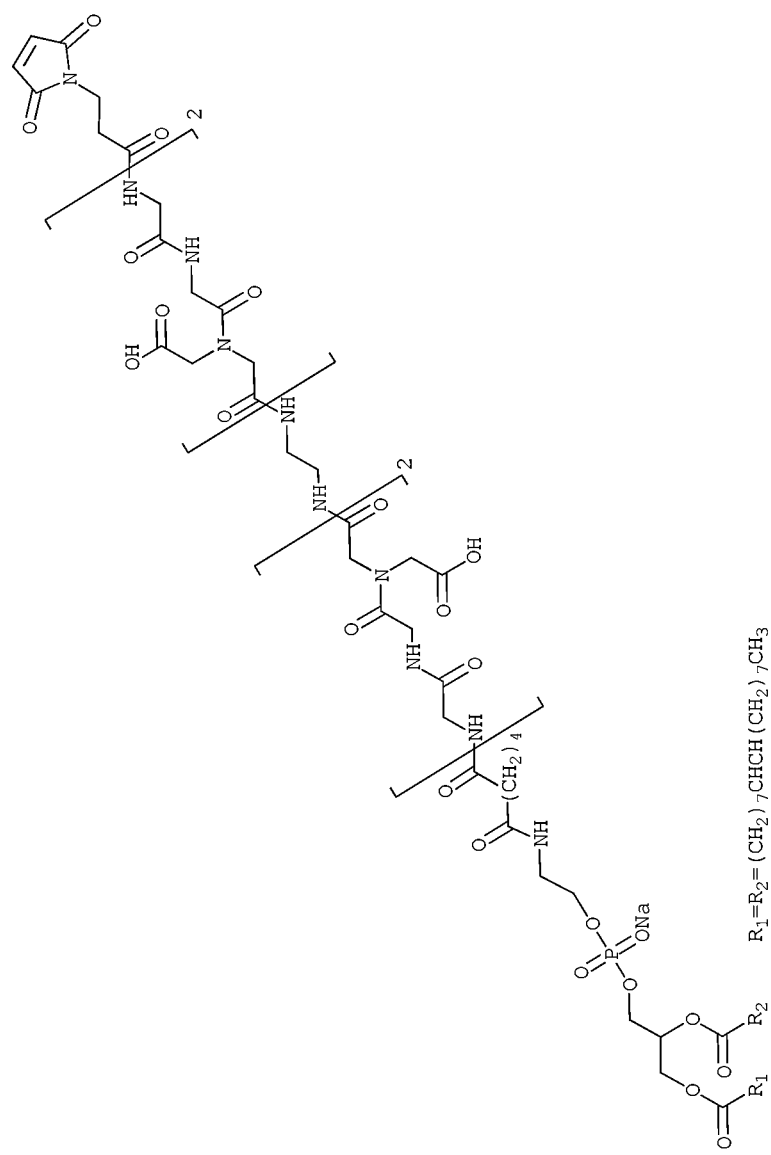
FIG. 1. Structure of the lipid conjugated maleimide designated FSL-RFG(Mal).
Figure 2:
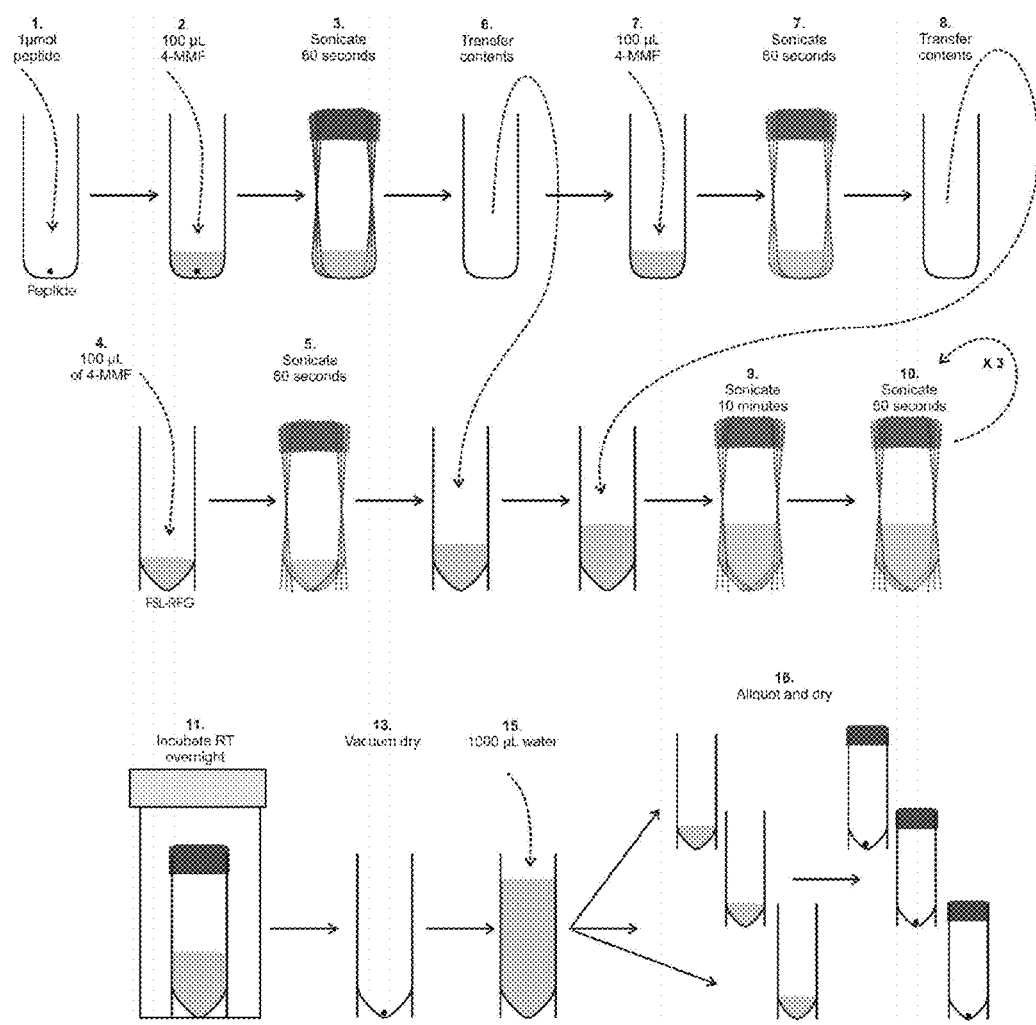
FIG. 2. Schematic overview of a method according to that described in the General Example.

Weinberg et al (2009) and Bovin et al (2009) both describe the preparation of peptide-lipid constructs for use in the preparation of kodecytes to be used in assays for the presence of reactive antibody. Both publications describe the preparation of peptide-lipid constructs via a lipid conjugated maleimide intermediate. Weinberg et al (2009) describes the preparation and use as the intermediate of a maleimido-derivative of DOPE-PEG$_6$-NH$_2$. Bovin et al (2009) describes the preparation and use as the intermediate of a construct designated FSL-RFG(Mal) (FIG. 1). This latter intermediate is prepared by the treatment of the construct designated DOPE-Ad-CMG(2)amine with a 5-fold excess of 3-maleimidopropionic acid oxybenztriazol ester in isopropanol-water.

Consistent with good laboratory practice the peptide-lipid constructs prepared by the methods disclosed in these publications are purified prior to their use in the preparation of the kodecytes required for use in diagnostic or prognostic assays. However, the step of purification by separation methods such as chromatography invariably results in losses of construct which is undesirable, particularly where the peptide is limited in amount, or the kodecytes to be prepared are only for experimental purposes.

In the method of the present invention the requirement for purification of the construct prior to use in the preparation of the kodecytes may be circumvented in part by the use of a reaction buffer that is removable by volatilization. The removal of the reaction buffer can be conveniently achieved in a biological laboratory, particularly if the primary focus of that laboratory is cell biology, by freeze-drying (lyophilisation).

Following incubation of the reaction mix and drying according to the method of the invention, the incorporation of the peptide-lipid construct into the membrane of the cell (kodecyte) or enveloped virus (kodevirion) serves as the separation step that has otherwise been achieved by the chromatography. The method of the invention circumvents the need for this intermediate purification step.

The method of the invention also permits the provision of a kit that may be conveniently employed in laboratories lacking equipment or experience in the purification of synthetic reaction products.

General Example

Step 1—Preparation of Reaction Mix

In accordance with the method of the invention a quantity of sulfhydryl (—SH) group containing peptide, e.g. a Cys containing peptide, sufficient to provide at least a 20% molar excess relative to the quantity of lipid conjugated maleimide to be used is prepared. Typically, synthetic peptides are supplied with quoted purities of >95% and a 20% excess should be sufficient for the reaction with the lipid conjugated maleimide to be complete. However, it will be recognised that quality and purity of peptides may vary between suppliers attributable to factors including cysteine (Cys) residue oxidation and small volume weighing errors. For these reasons users of the method of the invention may wish to employ up to a 100% molar excess of peptide relative to the quantity of lipid conjugated maleimide to be used to ensure near quantitative yield of peptide-lipid construct.

If necessary, spectrophotometric determination of reactive sulfhydryl content ($C_{SH}$) (μmol HS/mg) may be determined according to known procedures (Anon (2011)). If the determined $C_{SH}$ is too low the reduction of disulfide may be considered (Anon (2007)). The use of tributyl phosphine or TCEP should be avoided due to the reported reactivity with maleimide (Shafer et al (2000); Tyagarajan et al (2003)). If spectrophotometric determination of $C_{SH}$ is not performed users of the method of the invention are recommended to assume a purity of the synthetic peptide of no greater than 75% for the purpose of stoichiometric calculations (Cook (2006)).

It will be recognised from the foregoing that immunoglobulins are candidate sulfhydryl containing peptides that may potentially be used in the method of the invention. The indigenous disulfide groups in the hinge region of the immunoglobulin structure may be reduced with low concentrations of DTT, TCEP or MEA while leaving the disulfide bonds between the heavy and light chains relatively intact (Sun et al (2005)). As noted in Hermanson (2008) similar reduction can be done with F(ab'$_2$) fragments produced from the pepsin digestion of immunoglobulin G (IgG) molecules.

As noted elsewhere in this specification the phrase "sulfhydryl (—SH) group containing biomolecules" will be understood to encompass biomolecules where the requisite sulfhydryl group is natural, generated (i.e. by reduction of an existing disulfide) or introduced. Methods for the introduction of sulfhydryl groups in biomolecules using reagents such as N-acetyl, homocysteine thiolactone, AMBH, cystamine, SAMSA, SATA, SATP, SMPT and SPDP are known (Hermanson (2008)).

Irrespective of its source the quantity of sulfhydryl containing peptide is added to a volume of volatile reaction buffer (0.1 M 4-methylmorpholine formate (4-MMF) in 30% isopropanol (IPA) at a pH in the range 6.5 to 6.7) from a freshly opened, sealed vial and sonicated until a clear solution is obtained. An initial volume of 300 µl of the volatile reaction buffer is recommended for a quantity of peptide corresponding to 1 µmol (100% molar excess with respect to the lipid conjugated maleimide). The volatile reaction buffer should be stored degassed in a nitrogen atmosphere.

If necessary, but with caution, a further volume of buffer may be added or mixtures (1:1; v/v) of trifluoroethanol-volatile reaction buffer, hexafluroisopropanol-volatile reaction buffer, 2-methoxyethanol-volatile reaction buffer, trifluoroethanol-pyridine, hexafluoroisopropanol-pyridine, 2-methoxyethanol-pyridine, neat DMF or 6 guanidinium hydrochlorides may be used for dissolving peptides that otherwise prove insoluble at sufficiently high concentration.

Checking the extent of peptide solubility in the volatile reaction buffer before proceeding with the reaction is recommended. Note that DMSO should not be used to promote dissolution of the peptide as it may promote disulfide bond formation. Complete dissolution of the peptide is a prerequisite for successful reaction with the lipid conjugated maleimide.

An amount of the lipid conjugated maleimide (0.5 µmol) is reconstituted in a volume (100 µl) of the volatile reaction buffer from a freshly opened vial and following mixing by sonicating or vortexing for one minute a volume (300 µl) of the solution of peptide prepared as above added to the volume of lipid conjugated maleimide.

Step 2—Incubation the Reaction Mix

The reaction mix is sonicated in the sealed vial for 10 to 60 minutes in an ultrasonic bath. Typically, a clear solution will be obtained, but some partial precipitation may occur to provide a cloudy solution or fine suspension, particularly if the peptide being used is a basic peptide. In such circumstances periodic sonication over a period up to two hours should be sufficient to achieve adequate dissolution.

The mixture is incubated away from direct light for a time and temperature sufficient to allow all the lipid conjugated maleimide to react, e.g. overnight at room temperature (circa 25° C.).

Step 3—Drying the Reaction Mix

Optionally, the incubation is followed by the quenching of any possibly unreacted lipid conjugated maleimide by the addition of a non-interfering sulfhydryl containing compound such as cysteine (Cys), DTT, ME, etc. prior to freeze-drying. For example, the addition of a volume (60 µl) of 0.1 M mercaptoethanol may be added with stirring for at least one hour prior to the addition of 1 mL of water, freezing and drying.

Note that a vacuum centrifuge is not to be used. In addition, drying the reaction product using Fisher apparatus at elevated temperatures, or washing with absolute ether can yield a dried reaction product that is difficult to reconstitute in water.

For aliquoting and storage the dried reaction product is reconstituted in water by the addition of one drop of ethanol and a volume (1 mL) of water. Aliquots may then be freeze-dried as before in ready-to-use quantities. Immediate freeze-drying is recommended in the event the product is unstable in water or subject to degradation by abiotic or biotic factors. The reaction product following freeze-drying should be an amorphous white powder that is ready to use in the preparation of kodecytes.

Step 4—Contacting a Solution of the Reaction Product with a Surface

As noted above the method of the invention circumvents the need to purify the reaction product by separation methods (e.g. chromatography) and is therefore particularly convenient for use in a research laboratory with limited equipment, or equipment that is not suited to analytical and semipreparative scale purification. The reaction product is virtually free of by-products and contaminants that will interfere with the preparation of the kodecytes.

The preparation of kodecytes exploits the properties of synthetic constructs of the general structure F-S-L that are readily dispersible in biocompatible media; including saline, yet spontaneously incorporate into cell membranes. In effect, the purification is achieved in the method of the present invention by the incorporation of the construct in the cell membrane, any by-products and contaminants remaining dissolved in the suspending medium, e.g. a cell preservative (CELPRESOL™).

Kodecytes may be readily separated from the medium and washed without loss of construct as described elsewhere (Weinberg et al (2009); Bovin et al (2009)).

Presented with the Specific Example one could readily establish what variations to the exemplifying volatile reaction buffer (0.1 M 4-methylmorpholine formate (4-MMF) in 30% isopropanol (IPA) at a pH in the range 6.5 to 6.7) provided comparable results.

It is anticipated that volatile reaction buffers other than that specified above may be used. In addition to moderate variations in the concentrations of 4-MMF and IPA, these components of the reaction buffer may be substituted by other components. The amine (cationic) component (4-MMF) could be replaced by 4-ethylmorpholine, triethylamine, trimethylamine, N-methylpiperidine or N-methylpyrrolidine and the organic co-solvent (IPA), although preferred, could be replaced, at least in part, by n-propanol, ethanol, methanol, t-butanol, 2-methoxyethanol or trifluoroethanol. Where other co-solvents are included in the volatile reaction buffer the total concentration of co-solvent should be in the range 20 to 60%.

It is also anticipated that In addition to variations in the concentration of the components 4-MMF and IPA (and their substitution by other components) other buffering systems may be employed. However, trifluoroacetic acid (TFA) and hydrochloric acid (HCl) should not be used as components of these other buffering systems. These components (TFA and HCl) yield salts that are non-volatile at room temperature and are therefore best avoided. The molarity of the buffering system should be in the range 0.05 to 0.3 M and the pH in the range 5.8 to 7.5 when other buffering systems are employed.

Specific Example

The properties of a peptide-lipid construct and kodecytes prepared therefrom according to the method of the invention were compared with the properties of the same peptide-lipid construct (FSL-SYPH3) and kodecytes prepared therefrom according to known methods (Henry et al (2010)).

Materials

Blood group O packed red blood cells (RBCs) were washed with phosphate buffered saline (PBS). Washed RBCs were suspended in cell preservative (CELPRESOL™). PBS for the preparation of dilutions of constructs was filter sterilised. Stock solutions were prepared at a concentration of 200 μg/mL in PBS. Positive (POS) and negative (NEG) sera were chosen from a panel that had been previously determined by RPR, TPHA, and TPPA.

Methods and Results

A volume of 2 mL of filter sterilised PBS was added to a vial containing 400 μg of the construct designated FSL-SYPH3 to provide a stock solution of 200 μg/mL. The dispersion was vortexed and warmed to 37° C. for ten minutes. A stock solution of the construct designated FSL-RFG (Mal)-SYPH3 was similarly prepared at the same concentration.

Dilution series for each of the constructs were prepared at concentrations of 25, 50, 100 and 200 μg/mL. Equal volumes (30 μL) of the packed group O RBCs were added to and mixed with each of the dilutions of the dilution series for each construct in glass tubes. The tubes were then incubated in a water bath at 37° C. for 120 minutes with intermittent gentle mixing (three times) during the incubation period. The incubated RBCs were then washed two times with PBS and one time with cell preservative (CELPRESOL™).

A cell suspension was prepared by adding 492 μL of cell preservative (CELPRESOL™) to an 8 μL volume of washed, packed RBCs. An aliquot (30 μL) of the cell suspension and an aliquot (30 μL) of SYPH3 positive or negative sera were then added to a Coombs card chamber and incubated at 37° C. for 30 minutes before centrifugation at automatic setting of a microcentrifuge (DIAMED™).

Figure 3:
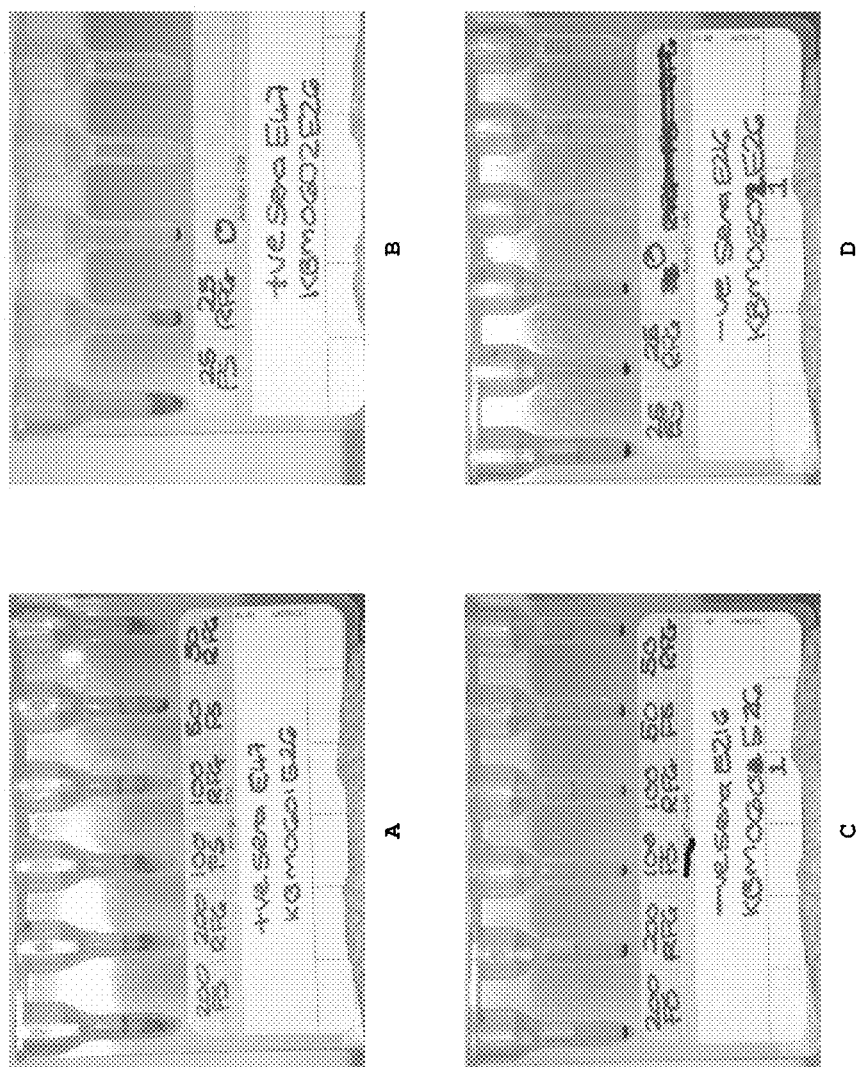
FIG. 3. Serology of kodecytes prepared as described in the Specific Example using SYPH positive sera E47 (3A and 3B) and SYPH negative sera E216 (3C and 3D). Abbreviations on gel cards correspond to kodecytes prepared using the construct designated FSL-SYPH3 (Henry et al (2010)) ('FS') and the construct designated FSL-RFG(Mal)-SYPH3 ('RFG').

A photograph of the card following centrifugation is presented as FIG. 3 of the drawings pages. Serology scores were recorded as negative or a positive (+1 to +3) reaction. The serology scores are recorded in Table 2. The serological performance of the kodecytes prepared according to the method of the present invention was indistinguishable from the performance of the kodecytes prepared by the known methods (Bovin et al (2009); Henry et al (2010)).

TABLE 1

| | | Concentration (μg/mL) | | | | |
|---|---|---|---|---|---|---|
| Construct | Sera | 200 | 100 | 50 | 25 | 0 |
| FSL-SYPH3 | POS E47 | +3 | +3 | +2 | +2 | 0 |
| FSL-RFG(MAL)-SYPH3 | POS E47 | +3 | +3 | +2 | +1 | 0 |

TABLE 1-continued

| | | Concentration (μg/mL) | | | | |
|---|---|---|---|---|---|---|
| Construct | Sera | 200 | 100 | 50 | 25 | 0 |
| FSL-SYPH3 | NEG E216 | 0 | 0 | 0 | 0 | 0 |
| FSL-RFG(MAL)-SYPH3 | NEG E216 | 0 | 0 | 0 | 0 | 0 |

The experiment was repeated including the construct designated FSL-RFG(Mal) to confirm the observed serology scores were not attributable to cross-reactivity with this construct. The serology scores (with no discrimination between positive serology scores) are recorded in Table 2.

Figure 4:
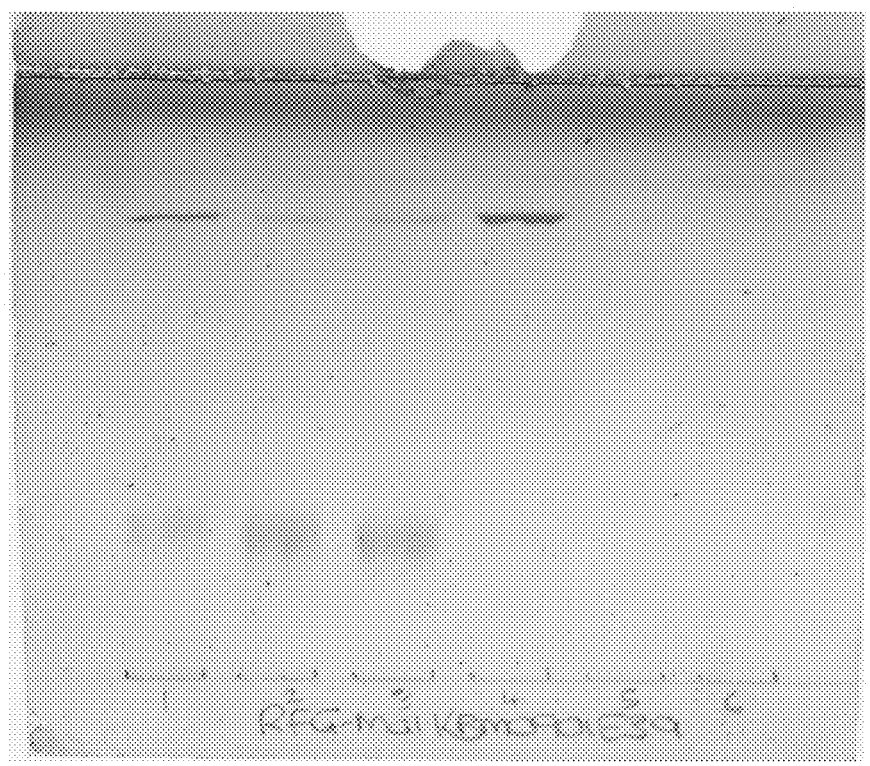
FIG. 4. Thin-layer chromatography of the peptide designated SYPH3 and samples from batches of the constructs designated FSL-SYPH3 (Henry et al (2010)), FSL-RFG (Mal) and FSL-RFG(Mal)-SYPH3: FSL-SYPH3 (Batch #1) [lane 1]; FSL-RFG(Mal)SYPH3 (Batch #1)[lane #2]; FSL-RFG(Mal)SYPH3 (Batch #2)[lane #3]; FSL-RFG(Mal) [lane #4]; SYPH3 peptide (diluted in 4MMF) [lane #5] and SYPH3 peptide (diluted in water) [lane #6].

Samples (4 μL) of the reagents and constructs used were applied at a concentration of 2 mg/mL in water to a thin layer chromatography (TLC) plate (ALUMGRA™ SIL G/UV silica 60) and eluted with 2:6:2 (v/v/v) chloroform/methanol/water containing 0.5% (v/v) pyridine. (The concentration of the construct designated FSL-RFG(Mal)-SYPH3 was based on the expected concentration of the construct excluding unreacted SYPH3 peptide.) The eluted TLC plate was visualised by spraying with a solution of anisaldehyde in acetic acid and heating to a temperature of 200° C. A photograph of the visualised plate is presented as FIG. 4 of the drawings pages. The chromatographic performance of the reagents and constructs was consistent with the construct designated FSL-SYPH3 and the construct designated FSL-RFG(Mal)-SYPH3 being identical.

Consistent with the provision of a General Example it will be appreciated that variations and modifications may be made to the steps of the method illustrated with reference to the Specific Example without departing from the scope of the invention. The advantages discussed in the description may be provided in the alternative or in combination in these other embodiments of the invention. Where known equivalents exist to specific features, such equivalents are incorporated as if specifically referred to in this specification. In particular, it will be understood that for a non-specific interaction, such as the interaction between the lipid (L) moiety of the constructs (F-S-L) and a surface such as a membrane, regioisomers and stereoisomers of naturally occurring lipids can be functionally equivalent. For example, it is contemplated that diacylglycerol 2-phosphate could be substituted for phosphatidate (diacylglycerol 3-phosphate) and that the absolute configuration of phosphatidate could be either R or S.

REFERENCES

Anon (2007a) BACHEM Technical Note.
Anon (2007b) *Reversal of Inadvertent Oxidation of Cys-containing Peptides* BACHEM Technical note.
Anon (2011) Sigma Technical Bulletins D130 and MBK1.
Bednar (1990) *Reactivity and pH dependence of thiol conjugation to N-ethylmaleimide: detection of a conformational change in chalcone isomerase Biochemistry*, 29(15), 3684-90.
Blake et al (2011) *FSL Constructs: A simple method for modifying cell/virion surfaces with a range of biological markers without affecting their viability* J. Vis. Exp. doi: 10.3791/3289.
Bovin et al (2009) Functional lipid constructs International patent application no. PCT/NZ2008/000266 (publ. no. WO 2009/048343).
Ellman (1959) *Tissue sulfhydryl group* Arch. Biochem. Biophys., 82, 70-77.

Gorin et al (1966) *Kinetics of the reaction of N-ethylmaleimide with cysteine and some congeners* Arch. Biochem. Biophys., 115, 593

Hayes et al (Eds.) (2009) *Biobased Surfactants and Detergents—Synthesis, Properties, and Applications* AOCS Press.

Henry et al (2010) Assays for serological detection of syphilis International patent application no. PCT/NZ2010/000111 (publ. no. WO 2010/143983).

Hermanson (Ed.)(2008) *Bioconjugate Techniques* Academic Press-Elsevier

Shafer et al (2000) *Reaction of Tris(2-carboxyethyl)phosphine (TCEP) with Maleimide and α-Haloacyl Groups: Anomalous Elution of TCEP by Gel Filtration* Analytical Biochemistry, 282, 161-4.

Smyth et al (1960) *Reactions of N-ethylmaleimide* J. Am. Chem. Soc., 82, 4600.

Smyth et al (1964) *Reaction of N-ethylmaleimide with peptides and amino acids* Biochem. J., 91, 589.

Tyagarajan et al (2003) *Thiol-reactive dyes for fluorescence labeling of proteomic samples* Electrophoresis, 24(14), 2348-58.

Weinberg et al (2009) Peptide lipid constructs and their use in diagnostic and therapeutic applications International application no. PCT/NZ2008/000239 (publ. no. WO 2009/035347).

TABLE 2

| Construct | Sera | Concentration (µg/mL) | | | | |
|---|---|---|---|---|---|---|
| | | 200 | 100 | 50 | 25 | 0 |
| FSL-SYPH3 | POS E47 | + | + | + | + | |
| FSL-RFG(MAL)-SYPH3 | POS E47 | + | + | + | + | |
| Nil | POS E47 | | | | | − |
| FSL-SYPH3 | POS E35 | + | − | | | |
| FSL-RFG(MAL)-SYPH3 | POS E35 | + | − | | | |
| FSL-RFG(MAL) | POS E35 | − | − | | | |
| NIL | POS E35 | | | | | − |
| FSL-SYPH3 | POS E36 | + | + | | | |
| FSL-RFG(MAL)-SYPH3 | POS E36 | + | + | | | |
| FSL-RFG(MAL) | POS E36 | − | − | | | |
| NIL | POS E36 | | | | | − |
| FSL-SYPH3 | POS E19 | | | | | |
| FSL-RFG(MAL)-SYPH3 | POS E19 | + | | | | |
| FSL-RFG(MAL) | POS E19 | − | | | | |
| NIL | POS E19 | | | | | − |
| FSL-SYPH3 | NEG E216 | − | − | − | − | |
| FSL-RFG(MAL)-SYPH3 | NEG E216 | − | − | − | − | |
| Nil | NEG E216 | | | | | − |
| FSL-SYPH3 | NEG E206 | − | − | | | |
| FSL-RFG(MAL)-SYPH3 | NEG E206 | − | − | | | |
| FSL-RFG(MAL) | NEG E206 | − | − | | | |
| Nil | NEG E206 | | | | | − |
| FSL-SYPH3 | NEG E226 | − | − | | | |
| FSL-RFG(MAL)-SYPH3 | NEG E226 | − | − | | | |
| FSL-RFG(MAL) | NEG E226 | − | − | | | |
| Nil | NEG E226 | | | | | − |
| FSL-SYPH3 | NEG E262 | − | | | | |
| FSL-RFG(MAL)-SYPH3 | NEG E262 | − | | | | |
| FSL-RFG(MAL) | NEG E262 | − | | | | |
| Nil | NEG E262 | | | | | − |
| FSL-SYPH3 | NEG E258 | − | | | | |
| FSL-RFG(MAL)-SYPH3 | NEG E258 | − | | | | |
| FSL-RFG(MAL) | NEG E258 | − | | | | |
| Nil | NEG E258 | | | | | − |

INDUSTRIAL APPLICABILITY

A facile method of localising sulfhydryl containing molecules to surfaces is disclosed. The method has particular application in biological laboratories where access to equipment for chemical purification is restricted or unavailable.

What we claim is:

1. A method of localising a biomolecule to a surface of a cell membrane comprising the steps:
    a) Mixing in a volatile reaction buffer a molar excess of the biomolecule with a lipid conjugated maleimide of the structure F-S-L to provide a reaction mix;
    b) Incubating the reaction mix for a time and at a temperature sufficient to allow all the lipid conjugated maleimide to have reacted with a sulfhydryl (—SH) group of the biomolecule to provide a reaction product;
    c) Freeze-drying the reaction product to remove the volatile reaction buffer and provide a dried product; and
    d) Contacting an aqueous solution of the dried product with the cell membrane,
    where:
    F is

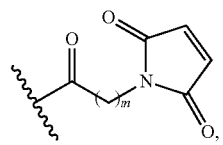

S is:

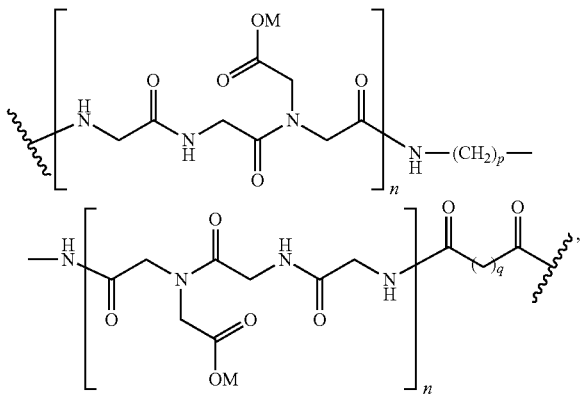

L is an amide linked diacyl- or dialkyl-glycerophospholipid, m is the integer 1, 2 or 3, M is a monovalent cation or substituent, n is the integer 1, 2 or 3, p is the integer 1, 2 or 3, q is the integer 3, 4 or 5, and the volatile reaction buffer consists essentially of 0.05 to 0.3M amine component in 20-60% organic co-solvent at a pH of 5.8 to 7.5 where the amine component is selected from the group consisting of 4-methylmorpholine formate, 4-ethylmorpholine, triethylamine, trimethylamine, N-methylpiperidine and N-methylpyrrolidone; and the organic co-solvent is selected from the group consisting of isopropanol, n-propanol, ethanol, methanol, t-butanol, 2-methoxyethanol and trifluoroethanol.

2. The method of claim 1 where the sulfhydryl (—SH) group is a cysteine residue (Cys).

3. The method of claim 2 where the biomolecule is a peptide.

4. The method of claim 3 where the biomolecule is a peptide with a cysteine residue (Cys) at or proximal to the C-terminus of the peptide.

5. The method of claim 4 where the biomolecule is a peptide with a cysteine residue (Cys) at the C-terminus.

6. The method of claim 5 where the surface is the cell membrane of a red blood cell.

7. The method of claim 1 where the incubating is for a time greater than 8 hours and at room temperature (circa 25° C.).

8. The method of claim 1 where the aqueous solution of the dried product is an aqueous saline solution of the dried product.

9. The method of claim 1 where the volatile reaction buffer is 0.1M 4-methylmorpholine formate (4-MMF) in 30% isopropanol (IPA) at a pH in the range 6.5 to 6.7.

10. The method of claim 1 where m is the integer 2.

11. The method of claim 1 where n is the integer 2.

12. The method of claim 1 where p is the integer 2.

13. The method of claim 1 where q is the integer 4.

14. The method of claim 1 where each of m, n and p are the integer 2 and q is the integer 4.

15. The method of claim 1 where L is an amide linked diacyl-glycerophospholipid.

16. The method of claim 15 where L is an amide linked phosphatidylethanolamine.

17. The method of claim 16 where L is 1,2-O-dioleoyl-sn-glycero-3-phosphatidylethanolamine (DOPE).

18. The method of claim 1 where
S is

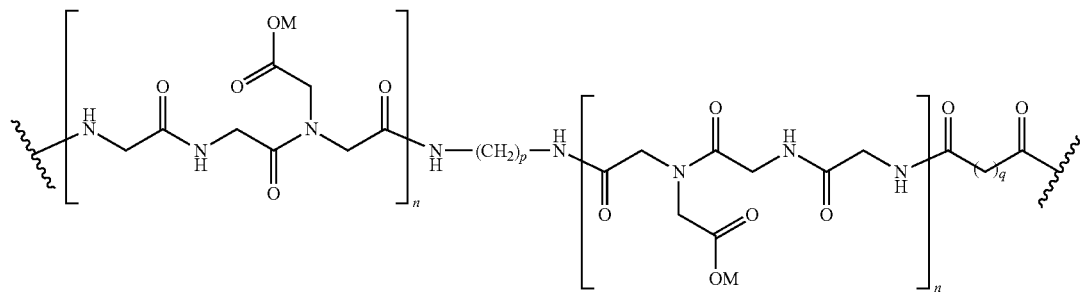

and
M is H or $CH_3$.

19. The method of claim 18 comprising the steps:
a) mixing in a reaction buffer of 0.1M 4-methylmorpholine formate (4-MMF) in 30% isopropanol (IPA) at a pH in the range 6.5 to 6.7, a molar excess of the peptide designated SYPH3 and a lipid conjugated maleimide of the structure:

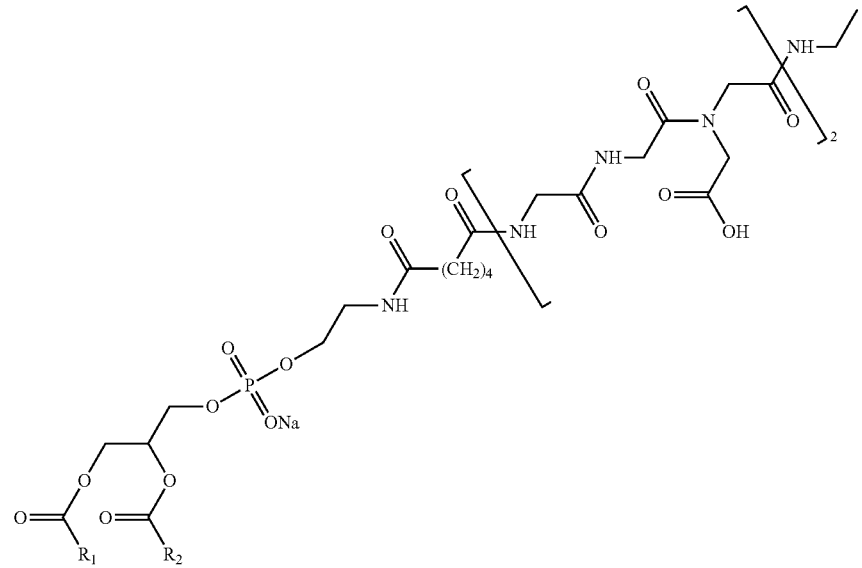

-continued

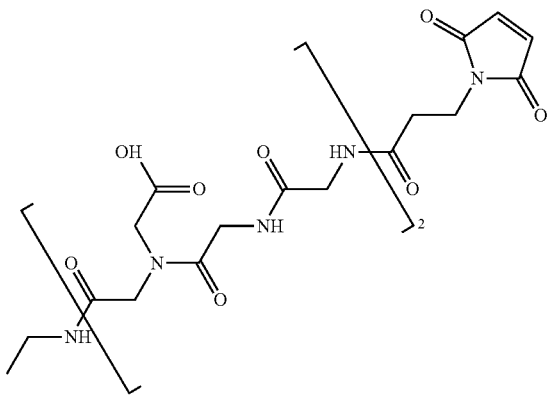

(where $R_1=R_2=(CH_2)_7CHCH(CH_2)_7CH_3$) to provide a reaction mix;

b) incubating the reaction mix for greater than 8 hours at room temperature (circa 25° C.) to provide a reaction product;

c) freeze-drying the reaction product to remove the reaction buffer and provide a dried product; and d) contacting an aqueous saline solution of the dried product with the cell membrane, where the cell is a red blood cell.

* * * * *